(12) United States Patent
Shih et al.

(10) Patent No.: US 7,537,629 B2
(45) Date of Patent: May 26, 2009

(54) POROUS METAL DENUDER

(75) Inventors: Tung-Sheng Shih, Taipei Hsien (TW); Chuen-Jinn Tsai, Hsinchu (TW); Cheng-Hsiung Huang, Hsinchu (TW)

(73) Assignee: Institute of Occupational Safety and Health, Council of Labor Affairs, Taipei Hsien (TW)

( * ) Notice: Subject to any disclaimer, the term of this patent is extended or adjusted under 35 U.S.C. 154(b) by 601 days.

(21) Appl. No.: 11/387,902

(22) Filed: Mar. 24, 2006

(65) Prior Publication Data

US 2009/0095161 A1    Apr. 16, 2009

Related U.S. Application Data

(63) Continuation-in-part of application No. 10/856,840, filed on Jun. 1, 2004, now abandoned.

(30) Foreign Application Priority Data

Jun. 30, 2003    (TW) .............................. 92117899 A

(51) Int. Cl.
*B01D 59/50*    (2006.01)
*G01N 1/22*    (2006.01)

(52) U.S. Cl. .................... 55/462; 55/482; 73/28.05; 73/863.22

(58) Field of Classification Search .................. 55/462, 55/465, 482; 73/28.05, 863.22
See application file for complete search history.

(56) References Cited

U.S. PATENT DOCUMENTS

| | | | |
|---|---|---|---|
| 3,693,457 A * | 9/1972 | Pilat ......................... 73/865.5 |
| 4,902,318 A | 2/1990 | Stevens et al. ........... 78/863.22 |
| 4,961,966 A | 10/1990 | Stevens et al. .............. 427/299 |
| 5,702,506 A | 12/1997 | Shih et al. ..................... 95/287 |
| 6,101,886 A * | 8/2000 | Brenizer et al. .......... 73/863.23 |
| 6,632,271 B2 | 10/2003 | Robertson et al. ............. 96/413 |
| 2001/0045000 A1 | 11/2001 | Gundel et al. ................. 29/458 |
| 2003/0015098 A1 | 1/2003 | Robertson et al. ............. 96/413 |
| 2004/0089079 A1 | 5/2004 | Engebretson ............ 73/863.23 |
| 2005/0045032 A1 | 3/2005 | Dasgupta et al. .............. 95/214 |

* cited by examiner

*Primary Examiner*—Robert A Hopkins
(74) *Attorney, Agent, or Firm*—Bacon & Thomas, PLLC

(57) ABSTRACT

A porous metal denuder has a cascade impactor to collect aerosol particles of different diameters, two porous metal discs downstream to collect basic and acidic gases, respectively, and a final filter to collect particles smaller than the cut diameter of the last stage of the cascade impactor which will penetrate the two porous metal discs.

10 Claims, 4 Drawing Sheets

POROUS METAL DENUDER

CROSS-REFERENCE TO RELATED APPLICATION

The present application is a continuation-in-part application of U.S. patent application Ser. No. 10/856,840, filed Jun. 1, 2004. The above-listed application is commonly assigned with the present invention and the entire contents of which are incorporated herein by reference.

BACKGROUND OF THE INVENTION

1. Field of the Invention

The present invention relates to a denuder for removing gases from an aerosol stream to measure their concentrations separately.

2. Description of the Related Art

An annular denuder system (ADS) uses a cyclone to remove particles greater than a certain diameter, at least one coated annular denuder tube to collect gases, and a filter which traps and collects particles. The coating on the inside surface of the annulus is a specially prepared resin absorbent for vapor absorption. A honey-comb denuder system (HDS) uses an impactor to remove particles having diameters greater than 2.5 μm from an inlet, and gases are collected by the two honey-combs coated with different chemical materials after the inlet.

The ADS and HDS can't classify particles of different diameters for further weighing and chemical analysis. The collection capacity of particles is limited since the substrates of the impaction plate of the HDS is made of flat plate and particle deposit on the plate can be reentrained easily. In addition, particles collected in the cyclone of the ADS are hard to retrieve for further weighing and chemical analysis. Furthermore, most prior art denuders can only be used for atmospheric sampling, and is not good for industrial environments with high pollutant concentrations.

Therefore, it is desirable to provide a porous metal denuder that is able to classify particles of different sizes, has high collection capacity for particles at impactor stages which use porous material as substrates, to use coated porous discs to collect gases of high concentration.

SUMMARY OF THE INVENTION

A primary objective of the present invention is to provide a porous metal denuder.

The porous metal denuder of the present invention is a new type of denuder, which utilizes a cascade impactor to classify aerosol particles with the cut-off aerodynamic diameter 10 μm at the first stage, and 2.5 μm at the $2^{nd}$ stage. More stages can be added to classify particles of smaller diameters. Both impactor stages use porous discs to increase the loading capacity of classified particles. Then the gas stream is passed through two coated porous metal discs having a pore size of about 100 μm to collect basic (ammonia) and acidic gases, respectively. The first porous disc is coated with citric acid while the second disc is coated with sodium carbonate to remove ammonia and acidic gases, respectively. Particles smaller than 2.5 μm from the cascade impactor will penetrate the two porous metal discs and be collected by a final filter.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
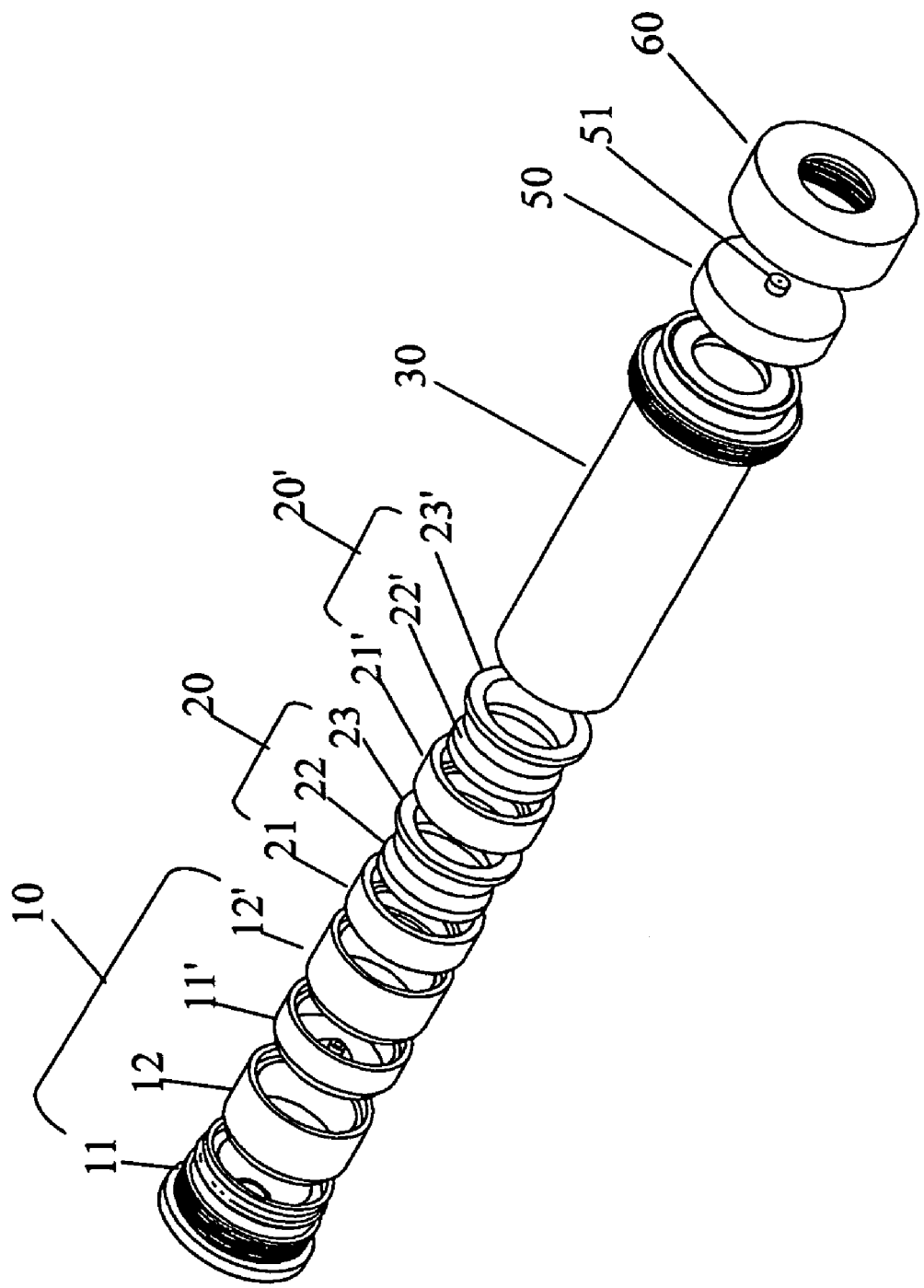
FIG. 1 is an exploded view of a porous metal denuder according to a first embodiment of the present invention.
Figure 2:
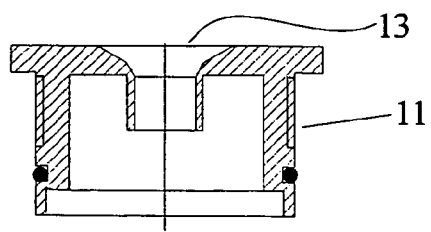
FIG. 2 is a cross-sectional view of the first stage nozzle 11, the first impactor 12, the second stage nozzle 11' and the second impactor 12' shown in FIG. 1.
Figure 2:
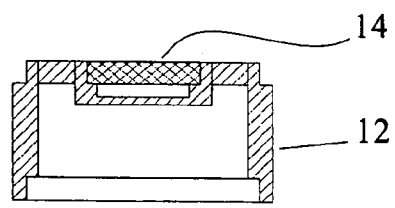
Figure 2:
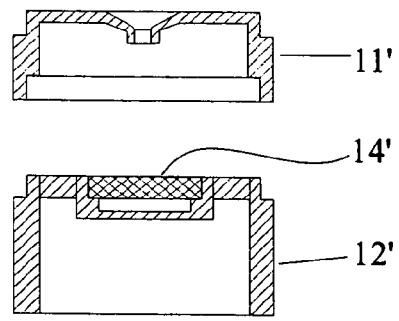
Figure 3:
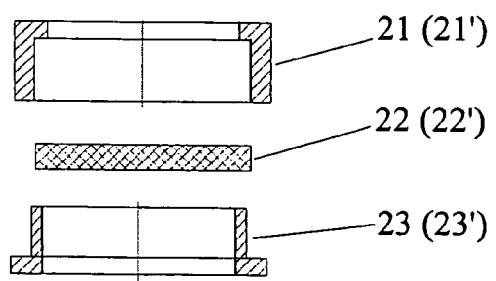
FIG. 3 is a cross-sectional view of the first (second) holder cover 21 (21'), the first (second) porous metal disc 22 (22'), and the first (second) holder base 23 (23') shown in FIG. 1.
Figure 4:
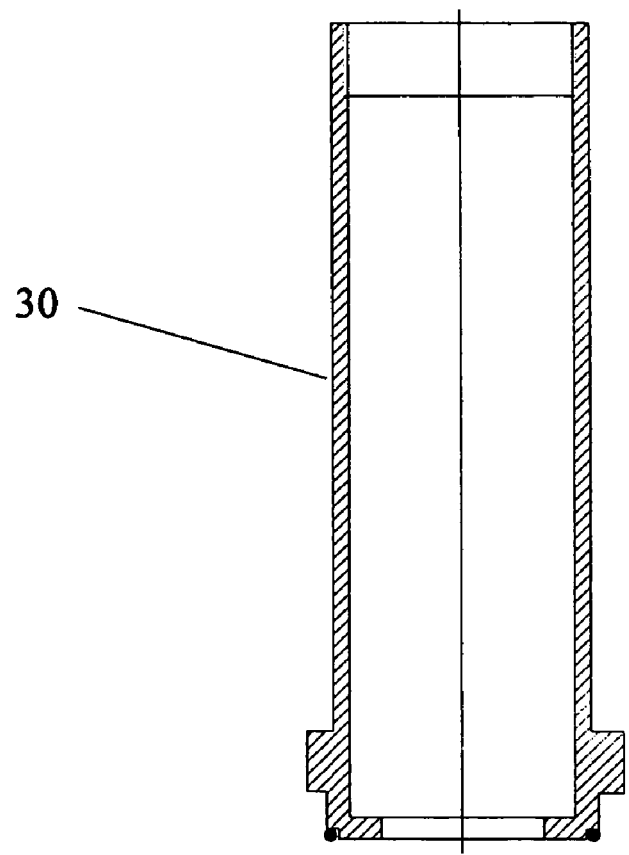
FIG. 4 is a cross-sectional view of the casing 30 shown in FIG. 1.
Figure 5:
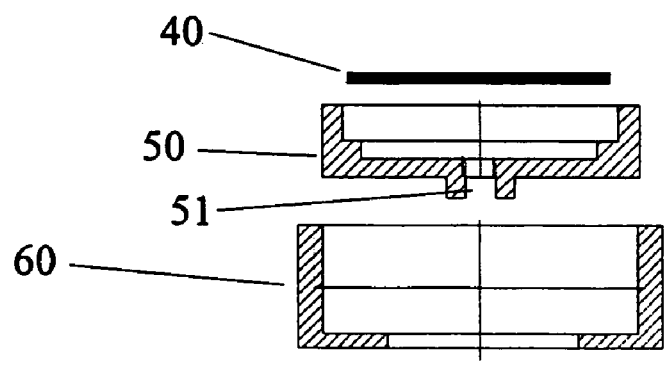
FIG. 5 is a cross-sectional view of the filter holder 50 and the cover 60 shown in FIG. 1, and a filter 40 clamped between the casing 30 and the filter holder 50 by the cover 60.

A porous metal denuder constructed in accordance with one of the preferred embodiments of the present invention is shown in FIGS. 1 to 5, which comprises a cascade impactor 10; a first collecting element 20; a second collecting element 20'; a casing 30; a filter 40; a filter holder 50 provided with an outlet 51; and a cover 60 which is adapted to be connected to a pump.

The cascade impactor 10 has a first stage nozzle 11 having an inlet 13, a first impactor 12, a second stage nozzle 11', and a second stage impactor 12'.

The first collecting element 20 has a first holder cover 21, a first porous metal disc 22, and a first holder base 23. The second collecting element 20' has a second holder cover 21', a second porous metal disc 22', and a second holder base 23', which are similar in structure to the first holder cover 21, the second porous metal disc 22 and the second holder base 23.

The first stage nozzle 11, the first impactor 12, the second stage nozzle 11', the second stage impactor 12', the first holder cover 21, the first holder base 23, the second holder cover 21', the second holder base 23', the casing 30 and the filter holder 50 all have a hollow tubular body and they are so constructed such that they are able to be substantially hermetically connected with one another in sequence, creating a path in the connected tubular bodies, and thus a gas stream can flow into the inlet 13 through the path and out from the outlet 51.

The first impactor 12 is provided with a first porous substrate 14 perpendicular to the path, so that the gas stream entering the inlet 13 will hit the first porous substrate 14 and flow around the first porous substrate 14, and aerosol particles larger than 10 μm entrained in the gas stream will be collected by the first porous substrate 14, part of particles will penetrate into the first porous substrate 14 to avoid piling up of a particle mound on the first porous substrate 14.

The second impactor 12' is provided with a second porous substrate 14' perpendicular to the path, so that the gas stream leaving the first impactor 12 will hit the second porous substrate 12' and flow around the second porous substrate 14', and aerosol particles larger than 2.5 μm in the gas stream will be collected by the second porous substrate 14', part of particles will penetrate into the second porous substrate 14' to avoid piling up of a particle mound on the second porous substrate 14'.

The first porous metal disc 22 is clamped between the first holder cover 21 and the first holder base 23, so that substantially all the gas stream leaving the second impactor 12' will contact and penetrate through the first porous metal disc 22, wherein the first porous metal disc 22 is coated with a chemical absorbent for absorbing acidic or basic gas entrained in the fluid steam. Similarly, substantially all the gas stream leaving the first collecting element 20 will contact and penetrate through the second porous metal disc 22', wherein the second porous metal disc 22' is coated with a chemical absorbent for absorbing acidic or basic gas entrained in the fluid steam.

The filter 40 is clamped between the casing 30 and the filer holder 50, so that substantially all the gas stream leaving the second collecting element 20' will contact and penetrate through the filter 40 before exiting the outlet 51, and aerosol particles not collected by the first porous substrate 14, the second porous substrate 14', the first porous metal disc 22 and the second porous metal disc 22' still can be collected by the filter 40.

Figure 6:
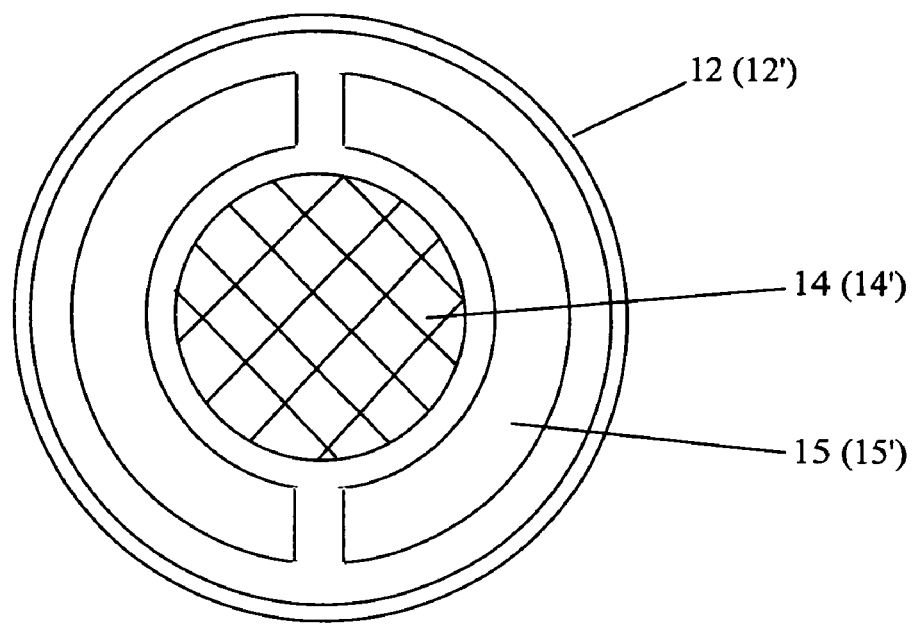
FIG. 6 is a top plan view of the first impactor 12 shown in FIG. 1.

As shown in FIG. 6, the first porous substrate 14 is supported at the center of the hollow tubular body of the first impactor 12 and gaps 15 are formed between the first porous substrate 14 and the hollow tubular body of the first impactor 12. The gaps 15 allow part of the gas stream flowing around the first impactor 12. Similar to the first porous substrate 14 and the first impactor 12 shown in FIG. 6, the second porous substrate 14' is also supported at the center of the hollow tubular body of the second impactor 12' and gaps 15' are formed between the second porous substrate 14' and the hollow tubular body of the second impactor 12'.

In this preferred embodiment the first stage nozzle 11, the first impactor 12, the second stage nozzle 11', the second stage impactor 12', the first holder cover 21, the first holder base 23, the second holder cover 21', the second holder base 23', the casing 30, the filter holder 50, and the cover 60 are made of Teflon®. The first porous substrate 14 and the second porous substrate 14' are a porous metal sheet having a thickness of about 0.3 cm and a pore size of about 100 µm. The first porous metal disc 22 and the second porous metal disc 22' have a thickness of about 0.3 cm and a pore size of about 100 µm. The absorbent on the first porous metal disc 22 and the absorbent on the second porous metal disc 22' is formed by drying the citric acid and sodium carbonate coating solution on the discs, respectively. The filter 40 is for collecting aerosol particles smaller than 2.5 µm.

A porous metal denuder constructed according to this preferred embodiment was tested. The sampling flow rate was 2 L/min. The first and the second porous metal discs (diameter: 2.54 cm; pore size: 100 µm; thickness 0.317 cm) to collect basic and acidic gases, respectively, were purchased from Mott Inc., Farmington, Conn., under a code of P/N 1000). The first and second impactor (having cut-off aerodynamic diameters of 9.5 and 2.0 µm, respectively) to collect aerosol particles have a diameter of 1.2 cm and other dimensions are the same as P/N 1000, Mott Inc. The denuder was tested for gas collection efficiency and capacity at a gas concentration of two times the permissible exposure limit (PEL, promulgated by Taiwan Institute of Occupational Safety and Health (IOSH), with relative humidity (RH) of 80±5% and temperature of 30±3° C. The test data indicate that the gas collection efficiency is high, and the capacity is sufficient for the acidic/basic gas sampling in the workplace. Using 5% (w/v, g/mL) sodium carbonate/1% (w/v) glycerol coating on the porous-metal disc, the collection efficiency is 91.2±0.26% (average±standard deviation), 95.08±0.06% and 100±04%, and the capacity is 4.47, 7.2, and 2.5 mg for $HNO_3$, HCl and HF, respectively. The collection efficiency for $NH_3$ for the porous-metal disc with 4% (w/v) citric acid coating is 96.39±0.13%, and the capacity is 33.6 mg.

The present invention shows that it is possible to use the porous metal disc in a personal denuder for sampling high concentrations of acidic and basic gases in the laboratory. The gas collection efficiency and capacity of the denuder with suitable coating material and concentration will be sufficiently high for the 8-hour sampling in the workplace, providing that the gas concentration is below the PEL.

Although the present invention has been explained in relation to its preferred embodiment, it is to be understood that many other possible modifications and variations can be made without departing from the spirit and scope of the invention as hereinafter claimed.

What is claimed is:

1. A porous-metal denuder comprising:
a cascade impactor comprising at least a first stage nozzle having an inlet, a first impactor, a second stage nozzle, and a second stage impactor,
a first gas collecting element comprising a first holder cover, a first porous metal disc, and a first holder base;
a second gas collecting element comprising a second holder cover, a second porous metal disc, and a second holder base;
a casing;
a filter; and
a filter holder provided with an outlet,
wherein the first stage nozzle, the first impactor, the second stage nozzle, the second stage impactor, the first holder cover, the first holder base, the casing and the filter holder all have a hollow tubular body and they are so constructed such that they are able to be substantially hermetically connected with one another in sequence, creating a path in the connected tubular bodies, and thus a gas stream can flow into the inlet through the path and out from the outlet,
wherein the first impactor is provided with a first porous substrate perpendicular to the path, so that the gas stream entering the inlet will hit the first porous substrate and flow around the first porous substrate, and aerosol particles larger than 10 µm in the gas stream will be collected by the first porous substrate, part of particles will penetrate into the first porous substrate to avoid piling up of a particle mound on the first porous substrate,
the second impactor is provided with a second porous substrate perpendicular to the path, so that the gas stream leaving the first impactor will hit the second porous substrate and flow around the second porous substrate, and aerosol particles larger than 2.5 µm in the gas stream will be collected by the second porous substrate, part of particles will penetrate into the second porous substrate to avoid piling up of a particle mound on the second porous substrate,
the first porous metal disc is clamped between the first holder cover and the first holder base, so that substantially all the gas stream leaving the second impactor will contact and penetrate through the first porous metal disc, wherein the first porous metal disc is coated with a first absorbent for absorbing basic gas entrained in the fluid steam,
the second porous metal disc is clamped between the second holder cover and the second holder base, so that substantially all the gas stream leaving the first porous metal disc will contact and penetrate through the second porous metal disc, wherein the second porous metal disc is coated with a second absorbent for absorbing acidic gases entrained in the fluid steam, and
the filter is clamped between the casing and the filer holder, so that substantially all the gas stream leaving the second porous metal disc will contact and penetrate through the filter before exiting the outlet, and aerosol particles smaller than 2.5 µm not collected by the cascade impactor, will penetrate the two porous metal discs and be collected by the filter.

2. The denuder of claim 1, wherein the first porous substrate is supported at the center of the hollow tubular body of the first impactor and gaps are formed between the first porous substrate and the hollow tubular body of the first impactor.

3. The denuder of claim 2, wherein the first porous substrate has a thickness of about 0.3 cm and a pore size of about 100 µm.

4. The denuder of claim 1, wherein the second porous substrate is supported at the center of the hollow tubular body of the second impactor and gaps are formed between the second porous substrate and the hollow tubular body of the second impactor.

5. The denuder of claim 4, wherein the second porous substrate has a thickness of about 0.3 cm and a pore size of about 100 µm.

6. The denuder of claim 1, wherein the first porous metal disc has a thickness of about 0.3 cm and a pore size of about 100 µm.

7. The denuder of claim 1, wherein the first absorbent on the first porous metal disc comprises citric acid.

8. The denuder of claim 1, wherein the second porous metal disc has a thickness of about 0.3 cm and a pore size of about 100 µm.

9. The denuder of claim 1, wherein the second absorbent on the second porous metal disc comprises sodium carbonate.

10. The denuder of claim 1, wherein the first stage nozzle, the first impactor, the second stage nozzle, the second stage impactor, the first holder cover, the first holder base, the second holder cover, the second holder base, the casing and the filter holder are made of Teflon®.

* * * * *